United States Patent [19]

Vega-Noverola et al.

[11] Patent Number: 5,026,858
[45] Date of Patent: Jun. 25, 1991

[54] PIPERIDINE DERIVATIVE

[75] Inventors: Armando Vega-Noverola; Jose Boix-Iglesias; Jose Prieto-Soto; Jacinto Moragues-Mauri, all of Barcelona, Spain

[73] Assignee: Walton S.A., Madrid, Spain

[21] Appl. No.: 720,295

[22] Filed: Apr. 5, 1985

Related U.S. Application Data

[63] Continuation of Ser. No. 425,705, Sep. 28, 1982, abandoned, which is a continuation of Ser. No. 852,074, Nov. 16, 1977, abandoned.

[30] Foreign Application Priority Data

Nov. 16, 1976 [GB] United Kingdom ............... 47739/76

[51] Int. Cl.$^5$ .................. C07D 211/58; A61K 31/445
[52] U.S. Cl. .................................................. 546/224
[58] Field of Search ......................................... 546/224

[56] References Cited

U.S. PATENT DOCUMENTS

| 3,342,826 | 9/1967 | Miller et al. | 546/224 |
| 3,577,440 | 5/1971 | Lunsford et al. | 260/326.3 |
| 3,963,745 | 6/1976 | Cale et al. | 260/326.5 S |
| 4,163,789 | 8/1979 | Mauri et al. | 546/224 |

FOREIGN PATENT DOCUMENTS

| 648164 | of 1964 | Belgium . | |
| 2705949 | 8/1977 | Fed. Rep. of Germany . | |
| 2751139 | 5/1978 | Fed. Rep. of Germany | 546/224 |
| 5916M | 4/1968 | France . | |
| 1019781 | 4/1964 | United Kingdom . | |
| 1574418 | 9/1980 | United Kingdom | 546/224 |

OTHER PUBLICATIONS

B. Costall et al., European Journal of Pharmacology, vol. 18, (1972), pp. 95-106.
Nils-Erik Anden et al., J. Pharm. Pharmac., (1973), vol. 25, pp. 346-348.
G. Bartholini, J. Pharm. Pharmac., (1976), vol. 28, pp. 429-433.
F. Sulser et al., Psychopharmacology, (1978), pp. 943-954.
Brenda Costall et al., European Journal of Pharmacology, (1980), vol. 66, pp. 207-215.
J. Prieto et al., J. Pharm. Pharmac., (1977), vol. 29, pp. 147-152.

*Primary Examiner*—Robert T. Bond
*Attorney, Agent, or Firm*—Spencer & Frank

[57] ABSTRACT

This invention relates to substituted benzoic acid amides of N-substituted piperidine and to pharmaceutical compositions thereof. The pharmaceutical compositions have served therapeutic uses, including treating nausea and vomiting, gastrointestinal disorders, and a variety of conditions affecting the central nervous system. The invention also relates to methods of preparing piperidine derivatives.

1 Claim, No Drawings

PIPERIDINE DERIVATIVE

This is a continuation of application Ser. No. 425,705 filed Sept. 28, 1982 now abandoned, which is a continuation of application Ser. No. 852,074 filed Nov. 16, 1977, now abandoned.

SUMMARY OF THE INVENTION

According to one aspect of our invention, we provide compounds of the general formula

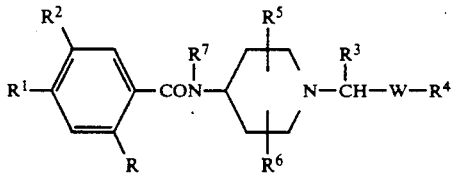

wherein R represents a halogen atom or a hydroxy, lower alkoxy, lower alkenyloxy, lower alkynyloxy or aralkyloxy (preferably a phenyl(lower)alkyloxy, e.g. benzyloxy) group, or a lower acyloxy group in which the acyl moiety is derived from a carboxylic acid (preferably a lower alkanoyloxy, e.g. acetoxy, group); $R^1$ represents a hydrogen atom or an amino, lower alkylamino, di(lower)alkylamino or a lower acylamino group in which the acyl moiety is derived from a carboxylic acid (preferably a lower alkanoylamino group); $R^2$ represents a nitro or trifluoromethyl group or a lower alkylthio or lower alkylsulphinyl group, or $R^1$ and $R^2$ together form a triazo group (i.e. —HN—N=N—); $R^3$ represents a hydrogen atom or a lower alkyl or lower alkenyl group, or a cycloalkyl or cycloalkenyl group having from 3 to 7 carbon atoms in the ring, or a phenyl group; $R^4$ represents a cycloalkyl group having from 3 to 7 carbon atoms in the ring, or an aroyl (e.g. benzoyl), aryl (e.g. phenyl or naphthyl) or heterocyclyl group (e.g. thienyl, pyridyl or pyrimidinyl); $R^5$, $R^6$ and $R^7$ each represent a hydrogen atom, a lower alkyl, lower alkenyl (e.g. —CH$_2$—CH=CH$_2$) or a benzyl group, and W represents a single bond or a lower alkylene (e.g. —CH$_2$— or —CH$_2$. CH$_2$—) or lower alkenylene (e.g. —CH=CH— or —CH$_2$—CH=CH—) group, with the proviso that when W is a single bond $R^3$ is other than a cycloalkenyl group, and pharmacologically-acceptable acid addition, alkali metal, alkaline earth metal and quaternary ammonium salts thereof, or N-oxide derivatives thereof.

The aryl group represented by $R^4$ may be a phenyl group of the general formula

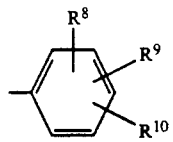

wherein $R^8$, $R^9$ and $R^{10}$ each represent a hydrogen or halogen atom, or a lower alkoxy, hydroxy, nitro, amino, lower alkylamino, lower dialkylamino, trifluoromethyl or lower alkyl group, or $R^8$ and $R^9$ together may form a methylenedioxy group in which case $R^{10}$ represents a hydrogen atom Preferred compounds of general formula I are those of the more specific formula

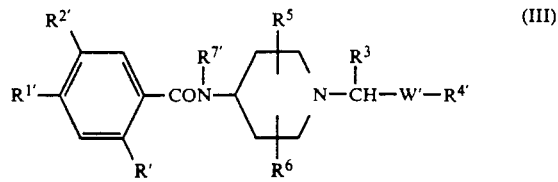

wherein $R^1$ represents a halogen (preferably chlorine) atom or a hydroxy, lower alkoxy (preferably methoxy or ethoxy), allyloxy, propargyloxy, acetoxy or benzyloxy group; $R^{1'}$ represents a hydrogen atom or an amino group or a lower acylamino group in which the acyl moiety is derived from a carboxylic acid (preferably acetamido) and $R^{2'}$ represents a nitro, methylsulphinyl or methylthio group, or $R^{1'}$ and $R^{2'}$ together form a triazo group; $R^{3'}$ represents a hydrogen atom, a lower alkyl (preferably methyl) or a phenyl group; $R^{4'}$ represents a cyclohexyl group or a phenyl group optionally substituted by one or two halogen atoms, lower alkyl or lower alkoxy groups, or by a methylenedioxy or trifluoromethyl group, or by three methoxy groups, or $R^{4'}$ represents a thienyl or naphthyl (preferably β-naphthyl) group or a benzoyl group optionally substituted by a halogen atom (preferably p-fluorobenzoyl); $R^{5'}$, $R^{6'}$ and $R^{7'}$ each represent a hydrogen atom or a lower alkyl group (preferably methyl or ethyl), and W' represents a single bond or a methylene, ethylene or vinylene group, and pharmacologically-acceptable acid addition salts thereof.

Of outstanding importance are those compounds of general formula III wherein R' represents a lower alkoxy (methoxy or ethoxy), allyloxy or propargyloxy group, $R^{1'}$ represents an amino group, $R^{2'}$ represents a nitro group, $R^{3'}$ represents a hydrogen atom, $R^{4'}$ represents a phenyl group optionally substituted by a halogen atom or a methyl or methoxy group (preferably in the para-position), $R^{5'}$, $R^{6'}$ and $R^{7'}$ each represent a hydrogen atom, and W' represents a methylene group or, preferably, a single bond.

Especially preferred compounds of the present invention are N-(1-benzylpiperid-4-yl)-2-methoxy-4-amino-5-nitrobenzamide, N-(1-p-methylbenzylpiperid-4-yl)-2-methoxy-4-amino-5-nitrobenzamide, N-(1-p-chlorobenzylpiperid-4-yl)-2-methoxy-4-amino-5-nitrobenzamide, N-(1-benzylpiperid-4-yl)-2-ethoxy-4-amino-5-nitrobenzamide and N-(1-phenethylpiperid-4-yl)-2-methoxy-4-amino-5-nitrobenzamide, and their pharmacologically-acceptable acid addition salts.

The qualification "lower" as applied in this specification to alkoxy, alkenyloxy, alkyl, alkythine, alkyoyloxy, alkylsulphinyl, alkanoyl, acyl, acyloxy, alkenyl, alkylene, and alkenylene groups means that the group in question contains at most 6 carbon atoms. It is to be understood that the cylcoalkenyl groups within definitions herein may have one, two, or three double bonds as is appropriate for the number of carbon atoms in the ring. The cycloalkenyl groups may be, for example, cyclopentenyl, cyclohexenyl or cycloheptenyl, with one double bond present, or cyclohexadienyl (preferably cyclohexa-1,4-dienyl optionally substituted by an alkyl group containing 1 to 3 carbon atoms), or cycloheptatrienyl.

According to another aspect of our invention, we provide compounds of the general formula

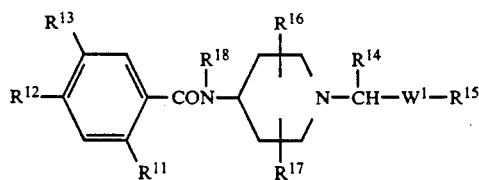

wherein $R^{11}$ represents a halogen atom or a hydroxy, lower alkoxy, lower alkenyloxy, lower alkynloxy or aralkyloxy (preferably phenyl(lower)alkyloxy, e.g. benzoyloxy) group, or a lower acyloxy group in which the acyl moiety is derived from a carboxylic acid (preferably a lower alkanoyloxy, e.g. acetoxy, group); $R^{12}$ represents a hydrogen atom or an amino, lower alkylamino, di(lower)alkylamino or a lower acylamino group in which the acyl moiety is derived from a carboxylic acid (preferably a lower alkanoylamino group), $R^{13}$ represents a nitro or trifluoromethyl group, or a lower alkylthio group, or $R^{12}$ and $R^{13}$ together form a triazo group (i.e. —HN—N=N—); $R^{14}$ represents a hydrogen atom or a lower alkyl or lower alkenyl group, or a cycloalkyl or cycloalkenyl group having from 3 to 7 carbon atoms in the ring, or a phenyl group; $R^{15}$ represents a cycloalkenyl group having from 3 to 7 carbon atoms in the ring optionally substituted by a lower alkyl or lower alkenyl group; $R^{16}$ $R^{17}$ and $R^{18}$ each represent a hydrogen atom, a lower alkyl, lower alkenyl (e.g. —CH$_2$—CH=CH$_2$) or a benzyl group, and $W^1$ represents a single bond or a lower alkylene (e.g. —CH$_2$— or —CH$_2$.CH$_2$—) or lower alkenylene (e.g. —CH=CH— or —CH$_2$—CH=CH—) group and pharmacologically acceptable acid addition, alkali metal, alkaline earth metal and quaternary ammonium salts thereof.

Preferred compounds of general formula I are those of the more specific formula

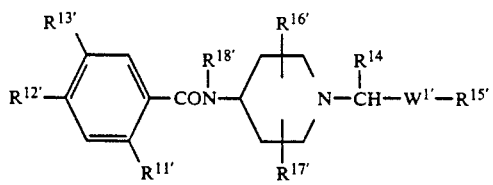

wherein $R^{11'}$ represents a halogen (preferably chlorine) atom or a hydroxy, lower alkoxy (preferably methoxy or ethoxy), allyloxy, propargyloxy, acetoxy or benzyloxy group; $R^{12'}$ represents a hydrogen atom, an amino group or a lower acylamino group in which the acyl moiety is derived from a carboxylic acid (preferably acetamido) and $R^{13'}$ represents a nitro or methylthio group, or $R^{12'}$ and $R^{13'}$ together form a triazo group; $R^{14'}$ represents a hydrogen atom or a lower alkyl (preferably methyl) group; $R^{15'}$ represents a cyclohexenyl (preferably cyclohex-3-enyl) or or a cyclohexadienyl (preferably cyclohexa-1,4-dienyl) group optionally substituted by a lower alkyl (preferably methyl) group, $R^{16'}$, $R^{17'}$ and $R^{18'}$ each represent a hydrogen atom or a lower alkyl (preferably methyl or ethyl) group and $W^{1'}$ represents a methylene group or, preferably, a single bond and pharmacologically-acceptable acid addition salts thereof.

Of outstanding importance are those compounds of general formula IIIa wherein $R^{11'}$ represents a lower alkoxy (preferably methoxy or ethoxy), allyloxy or propargyloxy group, $R^{12'}$ represents an amino group, $R^{13'}$ represents a nitro group, $R^{14'}$ represents a hydrogen atom, $R^{15'}$ represents a cyclohex-3-enyl group or, preferably, a cyclohexa-1,4-dienyl group optionally substituted by a methyl group, $R^{16'}$, $R^{17'}$ and $R^{18'}$ each represent a hydrogen atom, and $W^{1'}$ represents a methylene group or, preferably; a single bond.

Especially preferred compounds of the present invention are N-(1-cyclohexa-1',4'-dienyl-methylpiperid-4-yl)-2-methoxy-4-amino-5-nitrobenzamide, N-[1-(2-cyclohexa-1',4'-dienylethyl)piperid-4-yl]-2-methoxy-4-amino-5-nitrobenzamide, N-(1-cyclohexa-1',4'-dienyl-methylpiperid-4-yl)-2-ethoxy-4-amino-5-nitrobenzamide, N-[1-(4-methylcyclohexa-1,4-dienyl)methylpiperid-4-yl]-2-ethoxy-4-amino-5-nitrobenzamide and N-[1-(4-methylcyclohexa-1,4-dienyl)methylpiperid-4-yl]-2-methoxy-4-amino-5-nitrobenzamide, and their pharmacologically-acceptable acid addition salts.

As a further aspect of our invention, we provide pharmaceutical compositions comprising compounds of the general formulas I and Ia together with a pharmaceutically acceptable carrier or diluent.

DETAILED DESCRIPTION OF THE INVENTION

Preparation of Compounds

The compounds of general formula I can be prepared by the process which comprises reacting a reactive derivative of a benzoic acid of the general formula

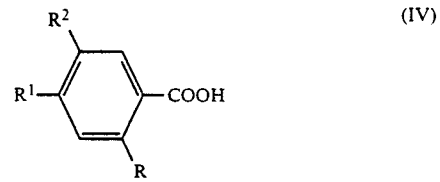

wherein R, $R^1$ and $R^2$ are as hereinbefore defined, with a piperidine derivative of the general formula

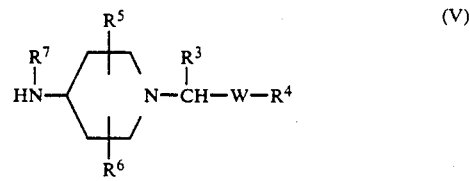

wherein the various symbols are as hereinbefore defined. The reactive derivative of the said benzoic acid may be a halide (preferably chloride), an alkyl ester (preferably methyl ester), an anhydride or a mixed anhydride.

The compounds of general formula Ia can be prepared by the process which comprises reacting a reactive derivative of a benzoic acid of the general formula

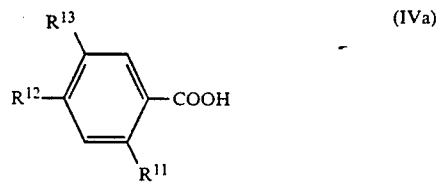

wherein $R^{11}$, $R^{12}$ and $R^{13}$ are as hereinbefore defined with a piperidine derivative of the general formula

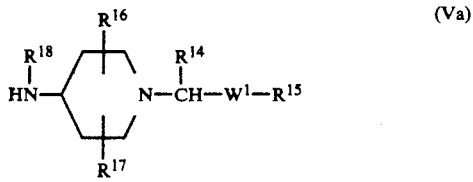

wherein the various symbols are as hereinbefore defined. The reactive derivative of the said benzoic acid may be a halide (preferably chloride), an alkyl ester (preferably methyl ester), an anhydride or a mixed anhydride.

The reactions are preferably carried out in the presence of an inert organic solvent, for example, benzene, toluene, chloroform, tetrahydrofuran, N,N-dimethylformamide or dioxan, at a temperature between about $-5°$ and $120°$ C.

Halides of a benzoic acid of general formula IV or IVa can be prepared by reaction of the acid with thionyl chloride or a phosphorus halide in the presence of an inert organic solvent such as benzene, toluene or a halogenated hydrocarbon. Mixed anhydrides of a benzoic acid of general formula IV or IVa can be prepared by the reaction of the acid with, for example, an alkyl chloroformate in the presence of an organic nitrogen-containing base, e.g., triethylamine, in an inert organic solvent, e.g., tetrahydrofuran N,N-dimethylformamide or methylene chloride, and at a temperature between about $-20°$ and $25°$ C. Esters and anhydrides of a benzoic acid of formula IV or IVa, which may be employed as starting materials in the aforementioned process, can be prepared from the benzoic acid by methods known per se, as can also the N-imidazolamides or acid azides of the acid.

The piperidine derivatives of general formula V wherein $R^7$ is a hydrogen atom can be prepared by reduction of corresponding 4-piperidone oximes with lithium aluminum hydride in the presence of diethyl ether or tetrahydrofuran, or by reductive amination of corresponding 4-piperidone oximes dissolved in an organic solvent, e.g., an alcohol containing from 1 to 4 carbon atoms, in the presence of platinum or Raney nickel as catalyst. The piperidine derivatives of general formula V wherein $R^7$ is a lower alkyl, a lower alkenyl or a benzyl group can be prepared from the corresponding N-acyl substituted compounds by reduction of the carbonyl group therein to methylene using lithium aluminum hydride.

The piperidine derivatives of general formula Va wherein $R^{18}$ is a hydrogen atom can be prepared by reduction of corresponding 4-piperidone oximes with lithium aluminium hydride in the presence of diethyl ether or tetrahydrofuran. The piperidine derivatives of general formula Va wherein $R^{14}$ and/or $R^{15}$ is or are a cyclohexadienyl group can be prepared from the corresponding compounds of general formula Va wherein $R^{14}$ and/or $R^{15}$ is or are a phenyl group by reduction with lithium in liquid ammonia or a lower alkylamine. The piperidine derivatives of general formula Va wherein $R^{18}$ is a lower alkyl, a lower alkenyl or a benzyl group can be prepared from the corresponding N-acyl substituted compounds by reduction of the carbonyl group therein to methylene using lithium aluminum hydride.

Other piperidine derivatives of general formulas V and Va can be prepared by methods known per se.

The piperidine derivatives of general formulas I and Ia can also be prepared by the direct reaction of a benzoic acid of general formula IV or IVa with a piperidine derivative of general formula V or Va, respectively, in the presence of an appropriate dehydrating agent. Such agents are, for example, silicon tetrachloride, a mono-, di- or trialkyl-silyl chloride, titanium tetrachloride, N,N'-dicyclohexyl-carbodiimide, thionyl chloride, sulphur trioxide in dimethyl sulphoxide, toluene-p-sulphonyl chloride, acetone dimethyl acetal or a polymeric dehydrating agent. The reaction is carried out in an inert organic solvent, e.g., methylene chloride, acetone, pyridine, ethyl acetate or dioxan, at a temperature between about $20°$ and $110°$ C.

The piperidine derivatives of general formula I or Ia wherein R or $R^{11}$ represents a hydroxy group are prepared, according to a further feature of the invention, from the corresponding O-methylated derivatives of general formula I or Ia (viz. R or $R^{11}$ represents a methoxy group) by the process which comprises the reaction of such compounds with boron tribromide or aluminium trichloride using methylene chloride or benzene as solvent medium at a temperature between about $20°$ and $80°$ C. The O-methylated compounds employed as starting materials in this process may be prepared by processes hereinbefore described using starting materials in which R or $R^{11}$ represents a methoxy group.

The piperidine derivatives of general formula I or Ia wherein R or $R^{11}$ represents a hydroxy group are also prepared, according to a still further feature of the invention, from the corresponding O-acylated derivatives of general formula I or Ia, viz. R or $R^{11}$ represents an acyloxy group. In this case the O-acylated derivatives are hydrolysed with dilute hychloric acid or with sodium or potassium hydroxide in an aqueous-alcoholic solution at a temperature between $20°$ and $90°$ C.

In the preparation of those compounds of general formula I or Ia wherein the symbol $R^1$ or $R^{12}$ represents an amino group, it is sometimes advisable to use as starting material corresponding compounds in which the amino group is protected by an acyl group, the acyl protecting group preferably being acetyl, chloroacetyl, trifluoroacetyl or phthaloyl. After the reaction the N-acylated intermediate products are subjected to acid or alkaline hydrolysis to give the corresponding compounds of general formula I or Ia in which $R^1$ or $R^{12}$ represents an amino group. Acid hydrolysis of the N-acylated compound may be carried out by heating with dilute hydrochloric acid, preferably at the boiling point of the reaction mixture, while alkaline hydrolysis is preferably carried out at a temperature between $20°$ and $90°$ C. with sodium or potassium hydroxide in an aqueous-alcoholic solution.

Therapeutic Properties and Administration

The piperidine derivatives of general formula I or Ia have as their principal pharmacological properties the ability to antagonize the effects of dopamine or dopaminergic agents of endogenous or exogenous origin and to cause stimulation of serotoninergic mechanisms. In those circumstances where homeostatic control is a balance between dopaminergic and serotoninergic mechanisms these two actions are synergistic and the precise contribution of each one to the final biological response is difficult to determine. As a group they have exhibited activities which may be considered beneficial in the treatment of a variety of cerebral malfunctions as well as obesity and gastrointestinal disturbances in mammals, including man. Their characteristic properties in experimental animals are antagonism of the effects of dopaminergic agents such as apomorphine, induction of catatonia, production of local anaesthesia, stimulation of gastrointestinal transit and induction of both spasmogenic and spasmolytic effects on smooth muscle according to the initial resting tone.

Nevertheless, as within the series antidopaminergic, serotoninergic and local anaesthetic potency do not necessarily run in parallel, the clinical applications of the various derivatives may well be different. As a group they may be useful in the treatment of a variety of conditions affecting the central nervous system such as acute and chronic psychosis, manic psychosis, schizophrenias, serious disturbances of behavior and non-melancholic depressive states and migraine, and be effective in the treatment of nausea and vomiting of diverse origin such as that resulting from gastrointestinal disorders, congestive heart failure, post-operative conditions, etc., as well as in the treatment of other gastrointestinal disorders such as dyspepsia, flatulance, bile regurgitation, hiatus hernia, peptic ulcer, reflux oesophagitis, gastritis, duodenitis and cholelithiasis. They may also be useful in the treatment of obesity and allied conditions where the administration of an appetite suppressant is warranted.

For therapeutic purposes the compounds of general formula I or Ia may be employed in the form of biologically and pharmacologically-acceptable inorganic or organic acid addition salts such as sulphates, hydrohalides (e.g., hydrochlorides), phosphates, lower alkanesulphonates, arylsulphonates and salts of aliphatic or aromatic acids containing from 1 to 20 carbon atoms which may contain one or more double bonds, or other functional groups such as hydroxy, lower alkoxy, amino or keto, e.g., fumarates.

The piperidine derivatives of general formula I or Ia wherein R or $R^{11}$ represents a hydroxy group may also form pharmacologically-acceptable salts with alkali or alkaline earth metals, which salts are formed by reaction of the derivatives of formula I or Ia wherein R or $R^{11}$ is a hydroxy group with an alkali metal or alkaline earth metal carbonate or hydroxide using water, methanol or ethanol, as solvent at a temperature between 40° and 100° C.

They may also be used for therapeutic purposes in the form of pharmacologically-acceptable quaternary ammonium salts such as those salts formed by reaction of the compounds of general formula I or Ia with lower alkyl halides or sulphates, or in the form of oxygenated derivatives in which oxygen is attached to the nitrogen atom of the piperidine nucleus, viz., the N-oxides.

The pharmacologically-acceptable acid addition salts and quaternary ammonium salts and N-oxides of the compounds of general formula I or Ia may be prepared by methods known per se, Included within the scope of the present invention are pharmaceutical compositions which comprise, as active ingredient, at least one compound of general formula I, or a pharmacologically-acceptable acid addition salt, alkali metal or alkaline earth metal salt or quaternary ammonium salt thereof or N-oxide thereof in association with a pharmaceutically acceptable carrier or diluent. Also included within the scope of the present invention are pharmaceutical compositions which comprise, as active ingredient, at least one compound of general formula Ia, or a pharmacologically acceptable acid addition salt, alkali metal or alkaline earth metal salt or quaternary ammonium salt thereof, in association with a pharmaceutically acceptable carrier or diluent. Preferably, the above compositions are made up in a form suitable for oral, topical, percutaneous or parenteral administration.

The pharmaceutically acceptable carriers or diluents which are admixed with the active compound, or compounds, to form the composition of this invention are well known per se and the actual excipients used depend, inter alia, on the method of administering the compositions. Compositions of the invention may be adapted for oral, topical, percutaneous, or parental administration; however, the preferred method of administration is per os. In this case, the compositions for oral administration may take the form of tablets, capsules, lozenges, or effervescent granules or liquid preparations, such as mixtures, clixirs, syrups, or suspensions, all containing one or more compounds of the invention; such preparations may be made by methods well known in the art.

The diluents which may be used in the preparation of the compositions include those liquid and solid diluents which are compatible with the active ingredients, together with, if desired, coloring or flavoring agents. Tablets or capsules may conveniently contain between about 0.1 and 20 mg, preferably between about 0.1 and 5 mg, of active ingredient or the equivalent amount of an acid addition salt or quaternary ammonium thereof, or N-oxide thereof.

The liquid compositions adapted for oral use may be in the form of solutions or suspensions. The solutions may be aqueous solutions of a soluble salt or other derivative of the active compound in association with, for example, sucrose to form a syrup. The suspensions may comprise an insoluble active compound of the invention or an acid addition, alkali metal or alkaline earth metal, or quaternary ammonium salt thereof in association with water, together with a suspending agent or flavoring agent.

Compositions for parenteral injection may be prepared from soluble salts, which may or may not be freeze-dried and which may be dissolved in water or an appropriate perenteral injection fluid.

In another aspect of the invention, the compounds may be mixed with other active anti-acid and anti-ulcer agents (excluding anti-cholinergic agents) for oral or, in appropriate cases, for parenteral use.

Useful tranquilizing and antiemetic dosages of the more interesting compounds appear to lie between 0.5 and 50 mg per day. Useful dosages for gastrointestinal tract indication also lie within the same range.

The pharmacological activity of certain of the compounds of the present invention has been measured and is set forth in the following tables:

TABLE 1

| | | | | | | | | | | | | | Dopamine [e] | Displacement [3H] Haloperidol[f] | |
|---|---|---|---|---|---|---|---|---|---|---|---|---|---|---|---|
| | | | | | | | | | | Anti-apomorphine[b] | | Ano- | Stomach | sensitive | | |
| R | $R^1$ | $R^2$ | $R^3$ | $R^4$ | $R^5$ | $R^6$ | $R^7$ | W | | rat | dog | rexia[c] | emptying[d] | aden-cyclase | straithum | limbic |
| [a]MeO | $NH_2$ | Cl | H | phenyl | H | H | H | — | | 2.5 | 40 | + | + | 5 | 25 | 5 |

TABLE 1-continued
PHARMACOLOGICAL ACTIVITY OF SOME COMPOUNDS OF FORMULA I

| R | R$^1$ | R$^2$ | R$^3$ | R$^4$ | R$^5$ | R$^6$ | R$^7$ | W | Anti-apomorphine$^{(b)}$ rat | dog | Ano-rexia$^{(c)}$ | Stomach emptying$^{(d)}$ | Dopamine $^{(e)}$ sensitive aden-cyclase | Displacement [3H] Haloperidol$^{(f)}$ straithum | limbic |
|---|---|---|---|---|---|---|---|---|---|---|---|---|---|---|---|
| " | " | NO$_2$ | H | " | " | " | " | — | 140 | <50 | + | + | 5 | 20 | 1 |
| " | " | " | H | " | " | " | " | CH$_2$ | 800 | >5000 | — | + | 1 | 10 | 1 |
| " | " | " | H | p-Me phenyl | " | " | " | — | ≃2 | <50 | + | + | | | |
| " | " | " | H | p-Cl phenyl | " | " | " | — | ≃2 | <50 | + | + | | | |
| EtO | " | " | H | phenyl | " | " | " | — | ≃100 | <50 | + | + | | | |
| AllylO | " | " | H | " | " | " | " | — | ≃300 | ≃100 | — | + | | | |
| Meto-clopra-mide | | | | | | | | | 13.6 | 450 | + | + | 60 | 150 | 150 |
| Sulpiride | | | | | | | | | >800 | 141 | — | — | 100 | 350 | 550 |

$^{(a)}$Reference standard (Clebopride hydrochloride).
$^{(b)}$Approximate oral ED$_{50}$ value for inhibition of apomorphine-induced gnawing behaviour in the rat (mg kg$^{-1}$) and vomiting in the dog ($\mu$g kg$^{-1}$)
$^{(c)}$Active (+) in causing significant inhibition of food intake (spaghetti) in screening test at 10 mg kg$^{-1}$ p.os in the mouse.
$^{(d)}$Active (+) in causing significant stomach emptying in screening test at 0.3 mg kg$^{-1}$ i.p. in the rat.
$^{(e)}$Approximate KI (nM) for inhibition of dopamine sensitive adenylate cyclase of rat straitum.
$^{(f)}$Approximate KI (nM) for displacement of [3H]-haloperidol from rat striatal and limbic forebrain membranes.

TABLE 2
PHARMACOLOGICAL ACTIVITY OF SOME COMPOUNDS OF FORMULA Ia

| | R$^{11}$ | R$^{12}$ | R$^{13}$ | R$^{14}$ | R$^{15}$ | R$^{16}$ | R$^{17}$ | R$^{18}$ | W$^1$ | Antiapomorphine$^{(b)}$ rat | dog | Stomach$^{(c)}$ emptying | Local$^{(d)}$ anaesthetic |
|---|---|---|---|---|---|---|---|---|---|---|---|---|---|
| $^{(a)}$ | MeO | NH$_2$ | Cl | H | phenyl | H | H | H | — | 2.5 | 40 | + | + |
| 2 | " | " | NO$_2$ | " | cyclohexyl dienyl | " | " | " | — | 60 | <50 | + | + |
| 3 | " | " | " | " | cyclohexyl dienyl | " | " | " | CH$_2$ | >300 | >500 | + | + |
| 4 | EtO | " | " | " | cyclohexyl dienyl | " | " | " | — | 50 | <50 | + | + |
| 5 | " | " | " | " | 4-Me cy-clohexyl-dienyl | " | " | " | — | 40 | <50 | + | + |
| 6 | MeO | " | " | " | 4-Me cy-clohexyl-dienyl | " | " | " | — | 35 | <50 | + | + |

$^{(a)}$Reference standard (Clebopride hydrochloride).
$^{(b)}$Approximate oral ED$_{50}$ value for inhibition of apomorphine-induced gnawing behaviour in the rat (mg kg$^{-1}$) and vomiting in the dog ($\mu$g kg$^{-1}$)
$^{(c)}$Active (+) in causing significant stomach emptying in screening test at 0.3 mg kg$^{-1}$ i.p. in the rat.
$^{(d)}$Active (+) at screening concentration of 0.5% w/v in blocking conduction in mouse sciatic nerve.

The following examples illustrate one aspect of the present invention, including preparation of piperidine compounds and pharmaceutical compositions.

EXAMPLE 1

To a solution of 2-methoxy-4-amino-5-nitrobenzoic acid (6.4 g; 0.03 moles) in N,N-dimethylformamide (175 ml) a solution of triethylamine (3 g; 0.03 moles) in N,N-dimethylformamide (5 ml) was added. The mixture was cooled to −5° to −10° C. and a solution of ethyl chloroformate (3.3 g; 0.03 moles) in N,N-dimethylformamide (5 ml) was added. The reaction mixture was stirred at the same temperature for 0.5 hours and then a solution of 1-benzyl-4-aminopiperidine (5.7 g; 0.03 moles) in N,N-dimethylformamide (15 ml) was added. After stirring for 1 hour at −5° to −10° C., the temperature was allowed to reach room temperature overnight. The solvent was removed in vacuo and the residue was poured into an aqueous sodium bicarbonate solution. The resulting solid was exhaustively extracted with methylene chloride, the organic layers washed with an aqueous sodium bicarbonate solution and then with water, dried (Na$_2$SO$_4$) and the solvent removed in vacuo. N-(1-Benzylpiperid-4-yl)-2-methoxy-4-amino-5-nitrobenzamide (9.3 g) was obtained and converted into its hydrochloride by treatment with a saturated solution of ethanolic hydrogen chloride; the hydrochloride melted at 218°-220° C. (dec).

The following compounds were prepared in a similar manner:

N-(1-cyclohexylmethylpiperid-4-yl)-2-methoxy-4-amino-5-nitrobenzamide, the hydrochloride of which melts at 215°-217° C. (dec);

N-[1-(1-phenylethyl)piperid-4-yl]-2-methoxy-4-amino-5-nitrobenzamide, the hydrochloride of which melts at 235°-236° C.;

N-(1-m-methylbenzylpiperid-4-yl)-2-methoxy-4-amino-5-nitrobenzamide, the hydrochloride monohydrate of which melts at 178°-180° C.;

N-(1-p-methylbenzylpiperid-4-yl)-2-methoxy-4-amino-5-nitrobenzamide, the hydrochloride of which melts at 202°-204° C.;

N-(1-p-chlorobenzylpiperid-4-yl)-2-methoxy-4-amino-5-nitrobenzamide, the hydrochloride of which melts at 238°-241° C. (dec);

N-[1-(2-methoxy-5-chlorobenzyl)piperid-4-yl]-2-methoxy-4-amino-5-nitrobenzamide, the fumarate of which melts at 219°-221° C. (dec);

N-[1-(3,4,5-trimethoxybenzyl)piperid-4-yl]-2-methoxy-4-amino-5-nitrobenzamide, the hydrochloride of which melts at 181°-183° C. (dec);

N-(1-phenethylpiperid-4-yl)-2-methoxy-4-amino-5-nitrobenzamide, the hydrochloride of which melts at 240°-242° C. (dec);

N-(1-cinnamylpiperid-4-yl)-2-methoxy-4-amino-5-nitrobenzamide, the fumarate of which melts at 236°–238° C. (dec);

N-methyl-N-(1-diphenylmethylpiperid-4-yl)-2-methoxy-4-amino-5-nitrobenzamide, the hydrochloride of which melts at 267°–269° C. (dec);

N-[1-(2-thienylmethyl)piperid-4-yl]-2-methoxy-4-amino-5-nitrobenzamide, the hydrochloride of which melts at 208°–210° C. (dec);

N-methyl-N-(1-benzylpiperid-4-yl)-2-methoxy-4-amino-5-nitrobenzamide, the fumarate of which melts at 141°–143° C.;

N-(1-benzyl-3-methylpiperid-4-yl)-2-methoxy-4-amino-5-nitrobenzamide, the fumarate of which melts at 210°–212° C.;

N-(1-m-trifluoromethylbenzylpiperid-4-yl)-2-methoxy-4-amino-5-nitrobenzamide, the hydrochloride monohydrate of which melts at 177°–179° C. (dec);

N-(1-benzylpiperid-4-yl)-2-methoxy-4-acetamido-5-nitrobenzamide, the fumarate of which melts at 204°–206° C.;

N-(1-p-methylbenzylpiperid-4-yl)-2-methoxy-4-acetamido-5-nitrobenzamide, the fumarate of which melts at 199°–200° C. (dec);

N-(1-p-chlorobenzylpiperid-4-yl)-2-methoxy-4-acetamido-5-nitrobenzamide, the fumarate of which melts at 186°–188° C. (dec);

N-[1-(2-methoxy-5-chlorobenzyl)piperid-4-yl]-2-methoxy-4-acetamido-5-nitrobenzamide, the fumarate of which melts at 191°–193° C.;

N-[1-(3,4,5-trimethoxybenzyl)piperid-4-yl]-2-methoxy-4-acetamido-5-nitrobenzamide, the fumarate of which melts at 220°–222° C. (dec);

N-[1-(1-phenylethyl)piperid-4-yl]-2-methoxy-4-acetamido-5-nitrobenzamide, the fumarate of which melts at 213°–214° C.;

bis[N-(1-phenethylpiperid-4-yl)-2-methoxy-4-acetamido-5-nitrobenzamide] fumarate, m.p. 209°–211° C. (dec);

N-(1-cinnamylpiperid-4-yl)-2-methoxy-4-acetamido-5-nitrobenzamide, the fumarate of which melts at 201°–203° C.;

N-[1-(2-thienylmethyl)piperid-4-yl]-2-methoxy-4-acetamido-5-nitrobenzamide, the fumarate of which melts at 203°–205° C.;

N-methyl-N-(1-benzylpiperid-4-yl)-2-methoxy-4-acetamido-5-nitrobenzamide, the fumarate of which melts at 142°–144° C.;

N-(1-cyclohexylmethylpiperid-4-yl)-2-methoxy-4-acetamido-5-nitrobenzamide, the fumarate of which melts at 217°–219° C.;

N-(1-benzylpiperid-4-yl)-2-methoxy-4,5-azimidobenzamide, the hydrochloride of which melts at 244°–246° C. (dec);

bis[N-(1-p-methylbenzylpiperid-4-yl)-2-methoxy-4,5-azimidobenzamide] fumarate, m.p. 243°–245° C. (dec);

bis[N-(1-p-chlorobenzylpiperid-4-yl)-2-methoxy-4,5-azimidobenzamide] fumarate, m.p. 214°–216° C. (dec);

N-[1-(1-phenylethyl)piperid-4-yl]-2-methoxy-4,5-azimidobenzamide, the fumarate of which melts at 203°–205° C.;

N-(1-cyclohexylmethylpiperid-4-yl)-2-methoxy-4,5-azimidobenzamide, the hydrochloride monohydrate of which melts at 239°–241° C.;

N-(1-benzylpiperid-4-yl)-2-methoxy-5-nitrobenzamide, the fumarate of which melts at 145°–147° C.;

N-(1-benzylpiperid-4-yl)-2-allyloxy-4-amino-5-nitrobenzamide, the fumarate of which melts at 191°–193° C.;

N-(1-cyclohexylmethylpiperid-4-yl)-2-allyloxy-4-amino-5-nitrobenzamide, the fumarate of which melts at 203°–205° C. (dec);

N-(1-benzylpiperid-4-yl)-2-propargyloxy-4-amino-5-nitrobenzamide, the fumarate of which melts at 213°–215° C. (dec);

N-(1-benzylpiperid-4-yl)-2-chloro-4-amino-5-nitrobenzamide, the fumarate of which melts at 226°–228° C. (dec);

N-(1-benzylpiperid-4-yl)-2-acetoxy-4-acetamido-5-nitrobenzamide, m.p. 191°–193° C.;

N-(1-benzylpiperid-4-yl)-2-hydroxy-4-acetamido-5nitrobenzamide, m.p. 220°–222° C.;

N-[1-(3-phenylpropyl)piperid-4-yl]-2-methoxy-4-amino-5-nitrobenzamide, the hydrochloride of which melts at 174°–176° C. (dec);

N-(1-cyclohexylmethyl-3-methylpiperid-4-yl)-2-methoxy-4-amino-5nitrobenzamide, the fumarate of which melts at 178°–180° C.;

N-(1-β-naphthylmethylpiperid-4-yl)-2-methoxy-4-amino-5-nitrobenzamide, the hydrochloride monohydrate of which melts at 185°–187° C.;

N-[1-(3-phenylpropyl)piperid-4-yl]-2-methoxy-4-acetamido-5-nitrobenzamide, the fumarate of which melts at 202°–204° C. (dec);

N-(1-benzylpiperid-4-yl)-2-propargyloxy-5-methylthiobenzamide, the fumarate of which melts at 175°–177° C.;

N-(1-benzylpiperid-4-yl)-2-hydroxy-5-methylthiobenzamide, the hydrochloride of which melts at 246°–248° C.;

N-(1-benzylpiperid-4-yl)-2-benzyloxy-5-methylthiobenzamide, the hydrochloride of which melts at 193°–195° C.;

N-(1-benzylpiperid-4-yl)-2-benzyloxy-5-methylsulphinylbenzamide, the hydrochloride of which melts at 166°–168° C.;

N-(1-p-methoxybenzylpiperid-4-yl)-2-methoxy-4-amino-5-nitrobenzamide, the hydrochloride of which melts at 220°–222° C. (dec);

N-(1-phenethylpiperid-4-yl)-2-propargyloxy-5-methylthiobenzamide, the fumarate of which melts at 196°–198° C. (dec);

N-(1-benzylpiperid-4-yl)-2-ethoxy-4-amino-5-nitrobenzamide, the fumarate of which melts at 228°–230° C. (dec);

N-[1-(3-p-fluorobenzoylpropyl)piperid-4-yl]-2-methoxy-4-amino-5-nitrobenzamide, the hydrochloride monohydrate of which melts at 222°–224° C. (dec);

N[1-(3,4-methylenedioxybenzyl)piperid-4-yl]-2-methoxy-4-amino-5-nitrobenzamide, the fumarate of which melts at 231°–233° C. (dec); and N-ethyl-N-(1-benzylpiperid-4-yl)-2-methoxy-5-nitrobenzamide, the hydrochlorideof which melts at 210°–212° C. (dec);

The fumarates mentioned above were obtained by adding fumaric acid in stoichiometric amount to a hot ethanolic solution of the piperidine base. The resulting hot solution was cooled and the fumarate crystallized.

EXAMPLE 2

A mixture of N-(1-benzylpiperid-4-yl)-2-acetoxy-4-acetamido-5-nitrobenzamide (1.4 g; 0.0031 moles) [prepared by the procedure described in Example 1], sodium hydroxide (0.3 g; 0.0062 moles), water (25 ml) and ethanol (12.5 ml) was boiled under reflux for 3 hours. Then the mixture was diluted with water, neutralized with diluted hydrochloric acid and the solid filtered off, washed with water and diethyl ether to give 1.1 g of N-(1-benzylpiperid-4-yl)-2-hydroxy-4-acetamido-5-nitrobenzamide, m.p. 220°–222° C.

EXAMPLE 3

A mixture of N-(1-benzylpiperid-4-yl)-2-hydroxy-4-acetamido-5-nitrobenzamide (1 g; 0.0024 moles) [prepared as described in Example 2], sodium hydroxide (0.2 g; 0.0048 moles), water (25 ml) and ethanol (12.5 ml) was boiled under reflux for 3 hours. Then the mixture was diluted with water, neutralized with diluted hydrochloric acid and the precipitate collected by filtration. This precipitate was washed with water and then with diethyl ether to give 0.9 g of N-(1-benzylpiperid-4-yl)-2-hydroxy-4-amino-5-nitrobenzamide. This compound was treated with a saturated solution of hydrogen chloride in methanol to give the hydrochloride which was recrystallized from ethanol. N-(1-Benzylpiperid-4-yl)-2-hydroxy-4-amino-5-nitrobenzamide hydrochloride was obtained, m.p. 248°–250° C. (dec).

EXAMPLE 4

A mixture of N-(1-benzylpiperid-4-yl)-2-methoxy-4-acetamido-5-nitrobenzamide (4.26 g; 0.01 mol) [prepared by the procedure described in Example 1], concentrated hydrochloric acid (5 ml), methanol (40 ml) and water (40 ml) was boiled under reflux for 2 hours. The solvent was removed in vacuo and the solid recrystallized from ethanol to give 3.4 g of N-(1-benzylpiperid-4-yl)-2-methoxy-4-amino-5-nitrobenzamide hydrochloride, m.p. 218°–220° C. (dec).

EXAMPLE 5

A suspension of N-(1-benzylpiperid-4-yl)-2-acetoxy-4-acetamido-5-nitrobenzamide (4.5 g; 0.01 mol) [prepared by the procedure described in Example 1] in ethanol (25 ml), concentrated hydrochloric acid (4.5 ml) and water (50 ml) was boiled under reflux for 2 hours. The mixture was diluted with water, made alkaline with sodium bicarbonate and extracted with chloroform. The organic solution was dried ($Na_2SO_4$), the solvent removed in vacuo and the residue triturated with diethyl ether to give a solid which was treated with a saturated solution of hydrogen chloride in ethanol. After crystallization from ethanol, 3 g of N-(1-benzylpiperid-4-yl)-2-hydroxy-4-amino-5-nitrobenzamide hydrochloride were obtained, m.p. 248°–250° C. (dec).

EXAMPLE 6

A solution of N-(1-benzylpiperid-4-yl)-2-methoxy-4-amino-5-nitrobenzamide (3.8 g; 0.01 mol) [prepared as described in Example 1] in methylene chloride (70 ml) was added to another solution of boron tribromide (2.84 ml; 0.03 moles) in methylene chloride (20 ml). The mixture was stirred at room temperature for 24 hours and then poured into a mixture of a saturated solution of sodium bicarbonate in water (250 ml) and methylene chloride (100 ml). The decanted organic solution was dried and the solvent removed in vacuo to give a paste which was triturated with petroleum ether. The residue obtained was treated with a saturated solution of ethanolic hydrogen chloride to give 3 g of N-(1-benzylpiperid-4-yl)-2-hydroxy-4-amino-5-nitrobenzamide hydrochloride, m.p. 248°–250° C. (dec).

EXAMPLE 7

N,N'-Dicyclohexylcarbodiimide (4.12 g; 0.02 moles) and 1-benzyl-4-aminopiperidine (3.8 g; 0.02 moles) were added successively to a solution of 2-methoxy-4-acetamido-5-nitrobenzoic acid (5.1 g; 0.02 moles) in methylene chloride (125 ml). After stirring overnight at room temperature, the insoluble N,N'-dicyclohexylurea was filtered off, the solution was washed with water, dried ($Na_2SO_4$) and the solvent removed in vacuo to give a solid. It was suspended in hot methanol and treated with the stoichiometric amount of fumaric acid to give a solution from which the N-(1-benzylpiperid-4-yl)-2-methoxy-4-acetamido-5-nitrobenzamide fumarate (6.2 g) crystallized. After recrystallization from methanol this compound melted at 204°–206° C.

EXAMPLE 8

A solution of 2-methoxy-4-acetamido-5-nitrobenzoyl chloride (8.2 g; 0.03 moles) dissolved in anhydrous tetrahydrofuran (45 ml) was added little by little to another solution of 1-benzyl-4-aminopiperidine (5.25 g; 0.028 moles) and triethylamine (3.87 ml; 0.028 moles) in anhydrous tetrahydrofuran (45 ml) at room temperature. On completion of the addition, the mixture was left at room temperature with stirring overnight and then the mixture was concentrated in vacuo, poured into water and extracted with chloroform. The organic solution was dried ($Na_2SO_4$) and the solvent removed in vacuo. The residue was suspended in hot methanol and treated with the stoichiometric amount of fumaric acid to give a solution from which the N-(1-benzylpiperid-4-yl)-2-methoxy-4-acetamido-5-nitrobenzamide fumarate (13.1 g) crystallized, m.p. 204°–206° C.

EXAMPLE 9

To a solution of N-(1-benzylpiperid-4-yl)-2-methoxy-4-amino-5-nitrobenzamide (3.8 g; 0.01 mole) [prepared as described in Example 1 or 4], in acetone (100 ml) and chloroform (100 ml), methyl iodide (1.25 ml; 0.02 moles) was added. After stirring at room temperature for 8 hours, an additional amount of methyl iodide (1.25 ml; 0.02 moles) was added and the mixture was left at room temperature for another 15 hours and then filtered. A solid was collected which was washed with diethyl ether to give 4.8 g of N-(1-benzylpiperid-4-yl)-2-methoxy-4-amino-5-nitrobenzamide methyl iodide. After recrystallization from a mixture of water-methanol, it melted at 232°–234° C. (dec).

EXAMPLE 10

To a solution of N-(1-benzylpiperid-4-yl)-2-methoxy-4-acetamido-5-nitrobenzamide (3.7 g; 0.0087 moles) [prepared by the procedure described in Example 1] in glacial acetic acid (25 ml) a 30% hydrogen peroxide solution (2.0 ml) was added. The mixture was heated for 12 hours at a temperature between 70° and 75° C., the solvent removed in vacuo and the residue was treated with water, made alkaline with diluted sodium hydroxide aqueous solution and extracted with methylene chloride. The organic solution was washed with water, dried ($Na_2SO_4$) and the solvent removed in vacuo to give a residue which was triturated with diethyl ether to give N-(1-benzylpiperid-4-yl)-2-methoxy-4-acetamido-5-nitrobenzamide N'-oxide (1.6 g), m.p. 184°–186° C. (dec).

EXAMPLE 11

50,000 capsules each containing 0.5 mg of N-(1-benzylpiperid-4-yl)-2-methoxy-4-amino-5-nitrobenzamide hydrochloride were prepared from the following formulation:

| | |
|---|---|
| N-(1-benzylpiperid-4-yl)-2-methoxy-4-amino-5-nitrobenzamide hydrochloride | 25 g |
| citric acid | 50 g |
| magnesium stearate | 5000 g |
| lactose spray dried | 11175 g |
| Pluronic F-68 | 2000 g |
| sodium lauryl sulphate | 1750 g |

Procedure

The N-(1-benzylpiperid-4-yl)-2-methoxy-4-amino-5-nitrobenzamide, citric acid, sodium lauryl sulphate, lactose and Pluronic F-68 were mixed together and passed through a screen with an opening of 0.6 mm. The magnesium stearate was added and the mixture encapsulated into gelatine capsules of appropriate size. Pluronic F-68 comprises a polyoxyethylated derivative of propylene glycol, available from Wyandotte Chemicals Corp.

EXAMPLE 12

100,000 tablets each containing 1 mg of N-(1-benzylpiperid-4-yl)-2-methoxy-4-amino-5-nitrobenzamide hydrochloride were prepared from the following formulation:

| | |
|---|---|
| N-(1-benzylpiperid-4-yl)-2-methoxy-4-amino-5-nitrobenzamide hydrochloride | 100 g |
| microcrystalline cellulose | 1850 g |
| lactose spray dried | 9820 g |
| carboxymethyl starch | 570 g |
| sodium stearyl fumarate | 80 g |
| colloidal silicon dioxide | 80 g |

Procedure

All the powders were passed through a screen with an opening of 0.6 mm. They were then all mixed in a suitable mixer for 30 minutes and compressed into 125 mg. tablets using 6 mm discs and flat bevelled punches. The disintegration time of the tablets was about 60 seconds.

EXAMPLE 13

10,000 suppositories each containing 1 mg of N-(1-benzylpiperid-4-yl)-2-methoxy-4-amino-5-nitrobenzamide hydrochloride were prepared as follows:

| | |
|---|---|
| N-(1-benzylpiperid-4-yl)-2-methoxy-4-amino-5-nitrobenzamide hydrochloride | 10 g |
| theobroma oil | 19990 g |

Procedure

The theobroma oil was melted and the active compound suspended in it. The mixture was then poured into appropriate suppository moulds to make 2.0 g suppositories.

EXAMPLE 14

50,000 ampoules each containing 0.5 mg of N-(1-benzyl-piperid-4-yl)-2-methoxy-4-amino-5-nitrobenzamide hydrochloride were prepared from the following formulation:

| | |
|---|---|
| N-(1-benzylpiperid-4-yl)-2-methoxy-4-amino-5-nitrobenzamide hydrochloride | 25 g |
| sodium chloride | 500 g |
| water injectable grade q.s. | 100 liters |

Procedure

The N-(1-benzylpiperid-4-yl)-2-methoxy-4-amino-5-nitrobenzamide hydrochloride and the sodium chloride were dissolved in approximately 80 liters of water with slight heating. The solution was diluted with water to 100 liters passed through a bacteria-retaining filter and filled into 2 ml glass ampoules in known manner. The production of the injectable solution can take place under sterile conditions. It is also possible to work under normal conditions and then to heat-sterilize the filled ampoules.

EXAMPLE 15

1,000 bottles (capacity 150 ml) each containing 15 mg of N-(1-benzylpiperid-4-yl)-2-methoxy-4-amino-5-nitrobenzamide hydrochloride were prepared as follows:

| | |
|---|---|
| N-(1-benzylpiperid-4-yl)-2-methoxy-4-amino-5-nitrobenzamide hydrochloride | 15 g |
| sorbitol | 70000 g |
| sorbic acid | 125 g |
| citric acid | 125 g |
| distilled water q.s. | 150 liters |
| flavouring agent | q.s. |

Procedure

The N-(1-benzylpiperid-4-yl)-2-methoxy-4-amino-5-nitrobenzamide hydrochloride and the sorbic acid were dissolved in 100 liters of water and then the sorbitol, citric acid and flavouring agent were added with stirring until dissolution. The mixture was diluted to 150 liters and divided amongst the bottles.

Similar compositions to those described in Examples 11 to 15 can be prepared having as the active ingredient piperidine derivatives of general formula I other than N-(1-benzylpiperid-4-yl)-2-methoxy-4-amino-5-nitrobenzamide, for example other products conforming to that formula mentioned in or at the end of Examples 1 to 10.

The following examples illustrate another aspect of the invention, including preparation of piperidine derivatives and pharmaceutical compositions.

EXAMPLE 16

To a solution of 2-methoxy-4-amino-5-nitrobenzoic acid (4.2 g; 0.02 moles) in N,N-dimethylformamide (400 ml) a solution of triethylamine (2.78 ml; 0.02 moles) in N,N-dimethylformamide (5 ml) was added. The mixture was cooled to −5° to −10° C. and a solution of ethyl chloroformate (2.2 g; 0.02 moles) in tetrahydrofuran (5 ml) was added. The reaction mixture was stirred at the same temperature for 2 hours and then a solution of 1-cyclohexa-1',4'-dienylmethyl-4-aminopiperidine (3.84 g; 0.02 moles) in tetrahydrofuran (15 ml) was added. After stirring for 1 hour at −5° to −10° C., the temperature was allowed to reach room temperature overnight. The solvent was removed in vacuo and the residue was poured into an aqueous sodium bicarbonate solution. The resulting solid was exhaustively extracted with methylene chloride, the organic layers washed with an aqueous sodium bicarbonate solution and then with water, dried (Na₂SO₄) and the solvent removed in vacuo. N-(1-Cyclohexa-1',4'-dienylmethylpiperid-4-yl)-2-methoxy-4-amino-5-nitrobenzamide (4.7 g) was obtained and converted into its hydrochloride by treatment with a saturated solution of ethanolic hydrogen chloride; the hydrochloride melted at 192°–194° C. (dec).

The following compounds were prepared in a similar manner:

N-[1-(1-cyclohexa-1',4'-dienylethyl)piperid-4-yl]-2-methoxy-4-amino-5-nitrobenzamide, the hydrochloride of which melts at 219°–221° C.;

N-methyl-N-(1-cyclohexa-1',4'-dienylmethylpiperid-4-yl)-2-methoxy-4-amino-5-nitrobenzamide, the fumarate of which melts at 205°–207° C. (dec);

N-(1-cyclohexa-1',4'-dienylmethylpiperid-4-yl)-2-methoxy-4-acetamido-5-nitrobenzamide, the fumarate of which melts at 184°–186° C.;

N-(1-cyclohexa-1',4'-dienylmethylpiperid-4-yl)-2-methoxy-4,5-azimidobenzamide, the fumarate of which melts at 178°–180° C. (dec);

N-(1-cyclohexa-1',4'-dienylmethylpiperid-4-yl)-2-methoxy-5-nitrobenzamide, the fumarate of which melts at 161°–163° C.;

N-(1-cyclohexa-1',4'-dienylmethylpiperid-4-yl)-2-ethoxy-4-amino-5-nitrobenzamide, the fumarate of which melts at 212°–214° C. (dec);

N-(1-cyclohexa-1',4'-dienylmethylpiperid-4-yl)-2-allyloxy-4-amino-5-nitrobenzamide, the fumarate of which melts at 198°–200° C.;

N-(1-cyclohexa-1',4'-dienylmethylpiperid-4-yl)-2-propargyloxy-4-amino-5-nitrobenzamide, the fumarate of which melts at 198°–200° C. (dec);

N-(1-cyclohexa-1',4'-dienylmethylpiperid-4-yl)-2-chloro-4-amino-5-nitrobenzamide, the fumarate of which melts at 201°–203° C. (dec);

bis[N-(1-cyclohexa-1',4'-dienylmethylpiperid-4-yl)-2-benzyloxy-5-methylthiobenzamide] fumarate, m.p. 154°–156° C.;

N-(1-cyclohex-3'-enylmethylpiperid-4-yl)-2-methoxy-4-amino- 5-nitrobenzamide, the fumarate of which melts at 201°–203° C.;

N-(1-cyclohex-3'-enylmethylpiperid-4-yl)-2-methoxy-4-acetamido-5-nitrobenzamide the fumarate of which melts at 204°–206° C. (dec);

N-(1-cyclohex-3'-enylmethylpiperid-4-yl)-2-methoxy-4-amino-5-nitrobenzamide, the fumarate of which melts at 220°–222° C.;

N-[1-(4-methylcyclohexa-1,4-dienyl)methylpiperid-4-yl]-2-chloro-4-amino-5-nitrobenzamide, the fumarate of which melts at 219°–221° C. (dec);

bis{N-[1-(4-methylcyclohexa-1,4-dienyl)methylpiperid-4-yl]-2-allyloxy-4-amino-5-nitrobenzamide} fumarate, m.p. 197°–199° C. (dec);

N-[1-(4-methylcyclohexa-1,4-dienyl)methylpiperid-4-yl]-2-ethoxy-4-amino-5-nitrobenzamide, the fumarate of which melts at 220°–222° C. (dec);

N-[1-(4-methylcyclohexa-1,4-dienyl)methylpiperid-4-yl]-2-methoxy-5-nitrobenzamide, the fumarate of which melts at 148°–150° C.;

N-[1-(4-methylcyclohexa-1,4-dienyl)methylpiperid-4-yl]-2-methoxy-4-amino-5-nitrobenzamide, the fumarate of which melts at 225°–227° C. (dec);

N-[1-(4-methylcyclohexa-1,4-dienyl)methylpiperid-4-yl]-2-propargyloxy-4-amino-5-nitrobenzamide, m.p. 185°–187° C.;

N-(1-cyclohexa-1',4'-dienylmethylpiperid-4-yl)-2-hydroxy-4-amino-5-nitrobenzamide, the fumarate of which melts at 233°–235° C. (dec);

N-(1-cyclohexa-1',4'-dienylmethylpiperid-4-yl)-2-acetoxy-4-acetamido-5-nitrobenzamide, m.p. 218°–220° C. (dec);

N-[1-(2-cyclohexa-1',4'-dienylethyl)piperid-4-yl]-2-methoxy-4-amino-5-nitrobenzamide, m.p. 215°–217° C.;

N-[1-(2-cyclohexa-1',4'-dienylethyl)piperid-4-yl]-2-ethoxy-4-amino-5-nitrobenzamide, m.p. 200°–202° C.;

N-[1-(2-cyclohexa-1',4'-dienylethyl)piperid-4-yl]-2-propargyloxy-4-amino-5-nitrobenzamide, m.p. 163°–165° C.;

N-(1-cyclohex-3'-enylmethylpiperid-4-yl)-2-allyloxy-4-amino-5-nitrobenzamide, m.p. 190°–192° C.;

N-(1-cyclohex-3'-enylmethylpiperid-4-yl)-2-ethoxy-4-amino-5-nitrobenzamido, the fumarate of which melts at 227°–229° C. (dec);

N-(1-cyclohexa-1',4'-dienylmethyl-3-methylpiperid-4-yl)-2-methoxy-4-amino-5-nitrobenzamide, the fumarate of which melts at 192°–194° C. (dec), and N-ethyl-N-(1-cyclohexa-1',4'-dienylmethylpiperid-4-yl)-2-methoxy-5-nitrobenzamide, the hydrochloride of which melts at 232°–234° C. (dec).

The fumarates mentioned above were obtained by adding fumaric acid in stoichiometric amount to a hot ethanolic solution of the piperidine base. The resulting hot solution was cooled and the fumarate crystallizes.

EXAMPLE 17

A mixture of N-(1-cyclohexa-1',4'-dienylmethypiperid-4-yl)-2-acetoxy-4-acetamido-5-nitrobenzamide (3.5 g; 0.007 moles) [prepared by the procedure described in Example 16], sodium hydroxide (0.75 g; 0.0155 moles), water (65 ml) and ethanol (35 ml) was boiled under reflux for 3 hours. Then the mixture was diluted with water, neutralized with dilute hydrochloric acid and the solid filtered off, washed with water and diethyl ether to give 2.6 g of N-(1-cyclohexa-1',4'-dienylmethylpiperid-4-yl)-2-hydroxy-4-acetamido-5-nitrobenzamide, m.p. 215°–217° C. (dec).

EXAMPLE 18

A mixture of N-(1-cyclohexa-1',4'-dienylmethylpiperid-4-yl)-2-hydroxy-4-acetamido-5-nitrobenzamide (2.1 g; 0.0050 moles) [prepared as described in Example 17], sodium hydroxide (0.40 g; 0.01 moles), water (50 ml) and ethanol (25 ml) was boiled under reflux for 3 hours. Then the mixture was diluted with water, neutralized with dilute hydrochloric acid and the precipitate collected by filtration. This precipitate was washed with water and then with diethyl ether to give 1.8 g of N-(1-cyclohexa-1',4'-dienylmethylpiperid-4-yl)-2-hydroxy-4-amino-5-nitrobenzamide. This compound was treated with fumaric acid by the procedure described at the end of Example 16 to give the N-(1-cyclohexa-1',4'-dienylmethylpiperid-4-yl)-2-hydroxy-4-amino-5-nitrobenzamide fumarate, m.p. 233°–235° C. (dec).

EXAMPLE 19

A mixture of N-(1-cyclohex-3'-enylmethylpiperid-4-yl)-2-methoxy-4-acetamido-5-nitrobenzamide (4.3 g; 0.01 mole) [prepared by the procedure described in Example 16], concentrated hydrochloric acid (5 ml), methanol (40 ml) and water (40 ml) was boiled under reflux for 2 hours. The methanol was removed in vacuo and the mixture made alkaline with an aqueous sodium bicarbonate solution. The solid was filtered off and N-(1-cyclohex-3'-enylmethylpiperid-4-yl)-2-methoxy-4-amino-5-nitrobenzamide (3.5 g) was obtained. The fumarate was prepared by the procedure described at the end of Example 16, m.p. 220°–222° C.

EXAMPLE 20

A suspension of N-(1-cyclohexa-1',4'-dienylmethylpiperid-4-yl)-2-acetoxy-4-acetamido-5-nitrobenzamide (4.56 g; 0.01 mole) [prepared by the procedure described in Example 16] in ethanol (30 ml), concentrated hydrochloric acid (4.5 ml) and water (60 ml) was boiled under reflux for 2 hours. The mixture was diluted with water, made alkaline with sodium bicarbonate and extracted with chloroform. The organic solution was dried (Na$_2$SO$_4$), the solvent removed in vacuo and the residue triturated with diethyl ether to give a solid which was treated with the stoichiometric amount of fumaric acid in hot ethanol. On cooling and further recrystallization from ethanol, 3.1 g of N-(1-cyclohexa-1',4'-dienylmethylpiperid-4-yl)-2-hydroxy-4-amino-5-nitrobenzamide fumarate were obtained, m.p. 233°–235° C. (dec).

EXAMPLE 21

A solution of N-(1-cyclohexa-1',4'-dienylmethylpiperid-4-yl)-2-methoxy-4-amino-5-nitrobenzamide (3.8 g; 0.01 mole) [prepared as described in Example 16] in methylene chloride (70 ml) was added to another solution of boron tribromide (2.84 ml; 0.03 moles) in methylene chloride (20 ml). The mixture was stirred at room temperature for 24 hours and then poured into a mixture of a saturated solution of sodium bicarbonate in water (250 ml) and methylene chloride (100 ml). The decanted organic solution was dried and the solvent removed in vacuo to give a paste which was triturated with petroleum ether. The residue obtained was treated with the stoichiometric amount of fumaric acid in hot ethanol to give 3.2 g of N-(1-cyclohexa-1',4'-dienylmethylpiperid-4-yl)-2-hydroxy-4-amino-5-nitrobenzamide fumarate, m.p. 233°–235° C. (dec).

EXAMPLE 22

N,N'-dicyclohexylcarbodiimide (4.12 g; 0.02 moles) and 1-cyclohexa-1',4'-dienylmethyl-4-aminopiperidine (3.8 g; 0.02 moles) were added successively to a solution of 2-methoxy-4-acetamido-5-nitrobenzoic acid (5.1 g; 0.02 moles) in methylene chloride (125 ml). After stirring overnight at room temperature, the insoluble N,N'-dicyclohexylurea was filtered off, the solution was washed with water, dried (Na$_2$SO$_4$) and the solvent removed in vacuo to give a solid. It was suspended in hot ethanol and treated with the stoichiometric amount of fumaric acid to give a solution from which the N-(1-cyclohexa-1',4'-dienylmethylpiperid-4-yl)-2-methoxy-4-acetamido-5-nitrobenzamide fumarate (5.9 g) crystallized. After recrystallization from methanol, this compound melted at 184°–186° C.

EXAMPLE 23

A solution of 2-methoxy-4-acetamido-5-nitrobenzoyl chloride (8.2 g; 0.03 moles) dissolved in anhydrous tetrahydrofuran (45 ml) was added little by little to another solution of 1-cyclohexa-1',4'-dienylmethyl-4-aminopiperidine. (5.25 g; 0.028 moles) and triethylamine (3.87 ml; 0.028 moles) in anhydrous tetrahydrofuran (45 ml) at room temperature. On completion of the addition, the mixture was left at room temperature with stirring overnight and then the mixture was concentrated in vacuo, poured into water and extracted with chloroform. The organic solution was dried (Na$_2$SO$_4$) and the solvent removed in vacuo. The residue was suspended in hot methanol and treated with the stoichiometric amount of fumaric acid to give a solution from which N-(1-cyclohexa-1',4'-dienylmethylpiperid-4-yl)-2-methoxy-4-acetamido-5-nitrobenzamide fumarate (12.8 g) crystallized, m.p. 184°–186° C.

EXAMPLE 24

To a solution of N-(1-cyclohexa-1',4'-dienylmethylpiperid-4-yl)-2-methoxy-4amino-5-nitrobenzamide (1.2 g; 0.0031 moles) [prepared as described in Example 16] in acetone (40 ml) and chloroform (40 ml), methyl iodide (1.25 ml; 0.02 moles) was added. After stirring at room temperature for 15 hours, the solid was collected and washed with diethyl ether to give 1.2 g of N-(1-cyclohexa-1',4'-dienylmethylpiperid-4-yl)-2-methoxy-4-amino-5-nitrobenzamide methyl iodide. After recrystallization from a mixture of water-methanol, it melts at 213°–215° C. (dec).

EXAMPLE 25

50,000 capsules each containing 0.5 mg of N-(1-cyclohexa-1',4'-dienylmethylpiperid-4-yl)-2-methoxy-4-amino-5-nitrobenzamide hydrochloride were prepared from the following formulation:

| | |
|---|---|
| N-(1-cyclohexa-1',4'-dienylmethylpiperid-4-yl)-2-methoxy-4-amino-5-nitrobenzamide hydrochloride | 25 g |
| citric acid | 50 g |
| magnesium stearate | 5000 g |
| lactose spray dried | 11175 g |
| Pluronic F-68 | 2000 g |
| sodium lauryl sulphate | 1750 g |

Procedure

The N-(1-cyclohexa-1',4'-dienylmethylpiperid-4-yl)-2-methoxy-4-amino-5-nitrobenzamide, citric acid, sodium lauryl sulphate, lactose and Pluronic F-68 were mixed together and passed through a screen with an opening of 0.6 mm. The magnesium stearate was added and the mixture encapsulated into gelatine capsules of appropriate size.

EXAMPLE 26

100,000 tablets each containing 1 mg of N-(1-cyclohexa-1',4'-dienylmethylpiperid-4-yl)-2-methoxy-4-amino-5-nitrobenzamide hydrochloride were prepared from the following formulation:

| | |
|---|---|
| N-(1-cyclohexa-1',4'-dienylmethylpiperid-4-yl)-2-methoxy-4-amino-5-nitrobenzamide hydrochloride | 100 g |
| microcrystaline cellulose | 1850 g |
| lactose spray dried | 9820 g |
| carboxymethyl starch | 570 g |
| sodium stearyl fumarate | 80 g |
| colloidal silicon dioxide | 80 g |

Procedure

All the powders were passed through a screen with an opening of 0.6 mm. They were then all mixed in a suitable mixer for 30 minutes and compressed into 125 mg tablets using 6 mm discs and flat bevelled punches.

The disintegration time of the tablets was about 60 seconds.

EXAMPLE 27

10,000 suppositories each containing 1 mg of N-(1-cyclohexa-1',4'-dienylmethylpiperid-4-yl)-2-methoxy-4-amino-5-nitrobenzamide hydrochloride were prepared as follows:

| | |
|---|---|
| N-(1-cyclohexa-1',4'-dienylmethylpiperid-4-yl)-2-methoxy-4-amino-5-nitrobenzamide hydrochloride | 10 g |
| theobroma oil | 19990 g |

Procedure

The theobroma oil was melted and the active compound suspend in it. The mixture was then poured into appropriate suppository moulds to make 2.0 g suppositories.

EXAMPLE 28

50,000 ampoules each containing 0.5 mg of N-(1-cyclohexa-1',4'-dienylmethylpiperid-4yl)-2-methoxy-4-amino-5-nitrobenzamide hydrochloride were prepared from the following formulation:

| | | |
|---|---|---|
| N-(1-cyclohexa-1',4'-dienylmethylpiperid-4-yl)-2-methoxy-4-amino-5-nitrobenzamide hydrochloride | 25 | g |
| sodium chloride | 500 | g |
| water injectable grade q.s. | 100 | liters |

Procedure

The N-(1-cyclohexa-1',4'-dienylmethylpiperid-4-yl)-2-methoxy-4-amino-5-nitrobenzamide hydrochloride and the sodium chloride were dissolved in approximately 80 liters of water with slight heating. The solution was diluted with water to 100 liters passed through a bacteria-retaining filter and filled into 2 ml glass ampoules in known manner.

The production of the injectable solution can take place under sterile conditions. It is also possible to work under normal conditions and then to heat-sterilize the filled ampoules.

EXAMPLE 29

1,000 bottles (capacity 150 ml) each containing 15 mg of N-(1-cyclohexa-1',4'-dienylmethylpiperid-4-yl)-2-methoxy-4-amino-5-nitrobenzamide hydrochloride were prepared as follows:

| | | |
|---|---|---|
| N-(1-cyclohexa-1',4'-dienylmethylpiperid-4-yl)-2-methoxy-4-amino-5-nitrobenzamide hydrochloride | 15 | g |
| sorbitol | 70000 | g |
| sorbic acid | 125 | g |
| citric acid | 125 | g |
| distilled water q.s. | 150 | liters |
| flavouring agent | | q.s. |

Procedure

The N-(1-cyclohexa-1',4'-dienylmethylpiperid-4-yl)-2-methoxy-4-amino-5-nitrobenzamide hydrochloride and the sorbic acid were dissolved in 100 liters of water and then the sorbitol, citric acid and flavouring agent were added with stirring until dissolution. The mixture was diluted to 150 liters and divided amongst the bottles.

Similar compositions to those described in Examples 25 to 89 can be prepared having as the active ingredient piperidine derivatives of general formula Ia other than N-(1-cyclohexa-1',4'-dienylmethylpiperid-4-yl)-2-methoxy-4-amino-5-nitrobenamide, for example, other products conforming to that formula mentioned at the end of Example 16 or in Examples 17 to 24.

What is claim is:

1. N-(1-cyclohexa-3'-enylmethylpiperid-4-yl)-2-ethoxy-4-amino-5-nitrobenzamide and pharmaceutically-acceptable acid addition salts thereof.

* * * * *